United States Patent
Zhou

(10) Patent No.: US 9,788,693 B1
(45) Date of Patent: Oct. 17, 2017

(54) APPARATUS FOR CLEANING HUMAN BODY ORIFICE

(71) Applicant: Zensun (Shanghai) Science & Technology, Co., Ltd., Shanghai (CN)

(72) Inventor: Mingdong Zhou, Shanghai (CN)

(73) Assignee: Zensun (Shanghai) Science & Technology Co., Ltd. (CN)

( * ) Notice: Subject to any disclaimer, the term of this patent is extended or adjusted under 35 U.S.C. 154(b) by 0 days.

(21) Appl. No.: 15/291,729

(22) Filed: Oct. 12, 2016

(30) Foreign Application Priority Data

May 9, 2016 (CN) .......................... 2016 1 0301432

(51) Int. Cl.
*A47K 7/04* (2006.01)
*A61C 17/34* (2006.01)
*A46B 13/00* (2006.01)
*A46B 13/04* (2006.01)
*A46B 5/00* (2006.01)

(52) U.S. Cl.
CPC ............ *A47K 7/043* (2013.01); *A46B 5/0095* (2013.01); *A46B 13/008* (2013.01); *A46B 13/04* (2013.01); *A61C 17/3481* (2013.01)

(58) Field of Classification Search
CPC ..... A61C 17/32; A61C 17/34; A61C 17/3436; A61C 17/222; A61C 17/3481; A61C 17/3409; A46B 13/008; A46B 9/028; A46B 11/063; A46B 11/066; A46B 13/001; A46B 13/02; A46B 13/04; A47K 7/043
USPC ........................ 15/22.4, 28, 179–180, DIG. 5
See application file for complete search history.

(56) References Cited

U.S. PATENT DOCUMENTS

| | | | |
|---|---|---|---|
| 572,459 A * | 12/1896 | Starritt | A61C 17/26 15/26 |
| 1,433,021 A | 10/1922 | Michael | |
| 2,588,000 A | 3/1952 | Hines | |
| 2,668,315 A * | 2/1954 | Crosby | A47L 5/24 15/339 |
| 3,024,883 A * | 3/1962 | Eriksson | A47L 17/00 15/28 |
| 3,289,239 A | 12/1966 | Diebold | |
| 4,041,568 A | 8/1977 | Rhodes | |
| 5,373,607 A | 12/1994 | Hwang | |
| 5,462,018 A | 10/1995 | Louison | |
| 6,171,268 B1 | 1/2001 | Zhadanov | |

(Continued)

FOREIGN PATENT DOCUMENTS

DE 19931156 A1 * 1/2001 ............... A46B 9/04

*Primary Examiner* — Laura C Guidotti
(74) *Attorney, Agent, or Firm* — Sterne, Kessler, Goldstein & Fox P.L.L.C.

(57) ABSTRACT

The present disclosure relates to an electric orifice cleaning brush including a brush head, a brush head mounting platform onto which the brush head is detachably mounted, and a motor holder for supporting the brush head mounting platform and accommodating a motor. The brush head includes a bristle implanting portion in the shape of a truncated cone and comprising a center region and bristles formed in bristle bindles. The bristle bindles are disposed outside the center region of the bristle implanting portion and are radially distributed in an evenly spaced manner. By means of the present disclosure, a complete cleaning of an orifice of a human body can be achieved, and damages to the orifice can be avoided.

16 Claims, 11 Drawing Sheets

(56) References Cited

U.S. PATENT DOCUMENTS

| | | | |
|---|---|---|---|
| 7,213,289 B2* | 5/2007 | Jaffe | A46B 5/0008 |
| | | | 15/23 |
| 7,363,673 B2 | 4/2008 | Schonewille et al. | |
| 7,478,457 B2 | 1/2009 | Kertz | |
| 8,484,788 B2 | 7/2013 | Brewer et al. | |
| 8,857,011 B2 | 10/2014 | Casper | |
| 2010/0049177 A1 | 2/2010 | Boone | |
| 2014/0013525 A1 | 1/2014 | Zhou | |
| 2014/0289978 A1 | 10/2014 | Serra-Garrido | |
| 2015/0173873 A1* | 6/2015 | Franke | A61C 17/3436 |
| | | | 15/29 |

* cited by examiner

APPARATUS FOR CLEANING HUMAN BODY ORIFICE

CROSS REFERENCE TO RELATED APPLICATION

This application claims priority to Chinese Patent Application No. CN201610301432.5, filed on May 9, 2016, which is hereby incorporated by reference in its entirety.

TECHNICAL FIELD

The present disclosure relates to an apparatus for cleaning human body orifice, more particularly, relates to an electric orifice cleaning brush.

BACKGROUND

In the embryo period, the umbilicus region is the only channel for an embryo to connect with its maternal body and get blood, oxygen and nutrition. Though after the fetus is given birth and the channel is cut off, the umbilicus region still has very close ties with the baby's organs. The umbilicus region is the thinnest part of the abdominal wall and has no subcutaneous fat. However, it has abundant blood vessels. Through scientific research, people have found that there are about 1400 kinds of bacteria parasitizing in human being's navels, more than 600 kinds of which are unknown. In our daily life, we seldom care about our navels, nor do we clean them frequently, which give very good opportunities for bacteria to live and proliferate. Different people have different types of navels, which can be classified into convex navels and concave navels. Especially, for a deeply concave navel, it is more prone to accumulate fouling inside, and it is very easy to get hurt and become infected when being cleaned off fouling.

These years, as people are paying more and more attention to human body aesthetics, they are more likely to choose the umbilical hole laparoscopic surgery as the abdominal surgery, which raises higher requirements for cleaning the umbilical hole.

At present, before surgery the umbilical hole is cleaned by manually dipping a dry cotton swab in turpentine, mainly rubbing the wrinkles on the wall of the umbilical hole and its bottom part, and repeatedly cleaning these parts using different cotton swabs until fouling cannot be observed. Due to the special anatomic structure of an umbilical hole, it is relatively difficult to be cleaned. The traditional way of cleaning using cotton swabs along with turpentine and alcohol may significantly irritate the skin of a patient. As a result, oftentimes red swelling of the skin can be observed. Also, it is not easy to use the thick head part of a cotton swab to clean the bottom part of a lacuna, and detachment of cotton flocks from the head part of the cotton swab may produce new foreign substances easily. Moreover, the traditional way of excavating longitudinally to clean the umbilical hole may have the potential risk of hurting the soft and tender skin at the bottom of the umbilical hole.

Further, in some other surgeries, it is also necessary to clean the patients' orifices. For example, for removal of earwax and foreign substances from ear, the traditional way of rinsing and excavating still poses certain risk to the interior structure of an ear. And some craniocerebral surgeries involving nasal cavity need to open surgical routes through the nasal cavity. However, current method of cleaning a nostril still has drawbacks, such as cleaning is incomplete and it may irritate the patient significantly. For surgeries involving the perineal region, such as abdominoperineal resection or repair of rectovaginal fistula, it is necessary to clean the perineal region. However, the anatomic structure of the perineal region, featuring plentiful wrinkles, as well as fecalith obstruction in the patient, may be the causes of incomplete cleaning of this region. And this also makes it very difficult to do surgical disinfection. With the advancement of surgical technologies, to reduce a patient's trauma and maintain the wholeness of the patient's skin as much as possible, surgeons use natural orifices of human bodies as surgical routes more and more frequently, so as to avoid large scale skin trauma. This kind of surgery is referred to as natural orifice transluminal endoscopic surgery (NOTES). However, as natural orifices of a human body are not like those exposed human organs, it is not easy to clean and disinfect these natural orifices. For these natural orifices, traditional ways of cleaning, such as rinsing, using cotton swabs and gauzes, also bring the similar problems such as incomplete cleaning and irritating the skin, etc., which occur in cleaning the umbilical hole.

SUMMARY

The present disclosure provides an electric orifice cleaning brush to solve the above-mentioned problems of not being able to completely clean human body orifices and easily hurting skin. The cleaning brush is suitable for patients who need to be cleaned and disinfected in various surgeries. Its main function is to clean off the persistent fouling on the body surface that are hard to get rid of. It is effective in cleaning some narrow recesses or orifices on the body surface, such as umbilical hole, armpit, ear hole, etc. The mechanism behind this product is, for example, producing friction with skin surface to break up fouling by way of vibration, while at the same time distributing disinfectants such as turpentine or alcohol across the body surface, thereby jointly achieving the goal of completely cleaning relevant parts. Its micro-vibration function is capable of facilitating the break-up of the fouling and more effectively dissolving it in the turpentine. Meanwhile, as no excessive longitudinal force will be produced in the course of vibration, the risk of cleaning umbilical hole can be reduced. The dense arrangement of brush bristles makes it easy to adsorb fouling. As a result, fouling will not be accumulated in the deep part of the umbilical hole. Also, material of extremely low dust-generation is chosen for producing brush bristles and thus, self-cleaning will not produce additional foreign substances.

In accordance with the one aspect of the present disclosure, an electric orifice cleaning brush is provided, which comprises a brush head, a brush head mounting platform onto which the brush head is detachably mounted, and a motor holder for supporting the brush head mounting platform and accommodating a motor; wherein the brush head comprises bristles and a bristle implanting portion, and after being formed bristle bundles are distributed in a substantially evenly spaced manner across the surface of the bristle implanting portion.

In some embodiments, the bristle implanting portion is substantially in the shape of a circular truncated cone.

In some embodiments, the bristle implanting portion is substantially in the shape of a circular rod.

In some embodiments, the bristle bundles are radially distributed.

In some embodiments, the bristle bundles are distributed in the form of a plurality of concentric circular rings or squares.

In some embodiments, there is no bristle bundle provided at the center region of the bristle implanting portion.

In some embodiments, there is no bristle implanting hole disposed at the center region of the bristle implanting portion.

In some embodiments, there is a protrusion disposed at the center region of the bristle implanting portion.

In some embodiments, there is no bristle bundle provided at the center region of the bristle implanting portion.

In some embodiments, there is a rigid sleeve disposed at the peripheral part of the brush head, for opening an orifice, while the bristle implanting portion is configured to be extendable and retractable relative to the rigid sleeve.

In some embodiments, the bristles are soaked with a solvent or a solution for adsorbing and dissolving matters to be cleaned off when in use.

In some embodiments, the distance between the bristle bundles is around 2.7 mm.

In some embodiments, the heights of the bristle bundles are gradually lowered along the radial direction, from the center of the bristle implanting surface to outside.

In some embodiments, the magnitude of reduction in the heights of the bristle bundles is uniform.

In some embodiments, the magnitude of reduction in the heights of the bristle bundles is gradually decreased.

In some embodiments, the bristle bundles are distributed in the shape of a truncated cone in a longitudinal section.

In some embodiments, the bristles are made from nylon fibers.

In some embodiments, the bristles are made from wools or pig hairs.

In some embodiments, the bristles are made from silica gel material, wherein each individual bristle constitutes a bundle.

In some embodiments, the tips of the bristle bundles are blunted.

In some embodiments, the heights of the bristle bundles are between 2 mm and 22 mm.

In some embodiments, the heights of the bristle bundles located at the peripheral region of the bristle implanting surface is so configured that they do not touch the skin of the person to be cleaned when the cleaning brush is being normally used.

In some embodiments, the depths of the bristle bundles implanted into the bristle implanting portion are 3 mm or more.

In some embodiments, the implanted portions of the bristle bundles are adhered by glue.

In some embodiments, the bristle bundles are stuck in bristle implanting holes after being bent by metal sheets.

In some embodiments, on the bristle implanting portion, there is an elastic hoop disposed at the opening of each bristle implanting hole.

In some embodiments, the bristle bundles have vivid colors.

In some embodiments, the bristle bundles are made from materials which are inherently colorful.

In some embodiments, the bristle bundles and the bristle implanting portion are integrally formed.

In some embodiments, the bristle implanting portion is clamped onto the brush head mounting platform.

In some embodiments, the motor drives the brush head to rotate.

In some embodiments, the motor further drives the brush head to vibrate up and down.

In some embodiments, the motor drives the brush head to rotate at a constant rate.

For example, the motor drives the brush head to vibrate up and down at different frequencies.

In some embodiments, the cleaning brush has a battery chamber.

In some embodiments, the cleaning brush has a dedicated power supply interface, for connection with an operation room energy platform.

In some embodiments, there is a power status indicator disposed on the housing of the cleaning brush.

In some embodiments, there is a selective multi-position switch disposed on the housing of the cleaning brush.

In accordance with the second aspect of the present disclosure, an electric orifice cleaning brush is provided, which comprises a brush head, a brush head mounting platform onto which the brush head is detachably mounted, and a motor holder for supporting the brush head mounting platform and accommodating a motor; wherein the brush head comprises bristles and a bristle implanting portion, the bristle implanting portion being substantially in the shape of a circular truncated cone, and after being formed the bristle bundles are distributed in a substantially evenly spaced manner across the surface of the bristle implanting portion, and wherein there is no bristle bundle at the center region of the bristle implanting portion, such that an empty region is formed; the empty region comprising no cavity structure (hole).

In accordance with the third aspect of the present disclosure, an electric orifice cleaning brush is provided, which comprises a brush head, a brush head mounting platform onto which the brush head is detachably mounted, and a motor holder for supporting the brush head mounting platform and accommodating a motor; wherein the brush head comprises bristles and a bristle implanting portion, the bristle implanting portion being substantially in the shape of a circular truncated cone, and after being formed the bristle bundles are radially distributed in a substantially evenly spaced manner across the surface of the bristle implanting portion, and wherein there is a protrusion structure disposed at the center region of the bristle implanting portion.

In accordance with the fourth aspect of the present disclosure, an electric orifice cleaning brush is provided, which comprises a brush head, a brush head mounting platform onto which the brush head is detachably mounted, and a motor holder for supporting the brush head mounting platform and accommodating a motor; wherein the brush head comprises bristles and a bristle implanting portion, the bristle implanting portion being substantially in the shape of a circular truncated cone, and after being formed the bristle bundles are radially distributed in a substantially evenly spaced manner across the surface of the bristle implanting portion, the heights of the bristle bundles are gradually lowered along the radial direction, from the center of the bristle implanting surface to outside, and wherein the heights of the bristle bundles located at the peripheral region of the bristle implanting surface is so configured that they do not touch the skin of the person to be cleaned when the cleaning brush is being normally used.

In accordance with the fifth aspect of the present disclosure, an electric orifice cleaning brush is provided, which comprises a brush head, a brush head mounting platform onto which the brush head is detachably mounted, and a motor holder for supporting the brush head mounting platform and accommodating a motor; wherein the brush head comprises bristles and a bristle implanting portion, and after being formed the bristle bundles are distributed in a substantially evenly spaced manner across the surface of the bristle implanting portion, and wherein on the bristle implanting portion, there is an elastic hoop disposed at the opening of each bristle implanting hole.

In accordance with the sixth aspect of the present disclosure, an electric orifice cleaning brush is provided, which comprises a brush head, a brush head mounting platform onto which the brush head is detachably mounted, and a motor holder for supporting the brush head mounting platform and accommodating a motor; wherein the brush head comprises bristles and a bristle implanting portion, and after being formed the bristle bundles are distributed in a substantially evenly spaced manner across the surface of the bristle implanting portion, and wherein the bristle bundles have vivid colors.

In accordance with the seventh aspect of the present disclosure, an electric orifice cleaning brush is provided, which comprises a brush head, a brush head mounting platform onto which the brush head is detachably mounted, and a motor holder for supporting the brush head mounting platform and accommodating a motor; wherein the brush head comprises bristles and a bristle implanting portion, and after being formed the bristle bundles are radially distributed in a substantially evenly spaced manner across the surface of the bristle implanting portion, and wherein there is a rigid sleeve disposed at the peripheral part of the brush head, for at least partly opening an orifice, while the bristle implanting portion is configured to be extendable and retractable relative to the rigid sleeve.

In accordance with the eighth aspect of the present disclosure, an electric orifice cleaning brush is provided, which comprises a brush head, a brush head mounting platform onto which the brush head is detachably mounted, and a motor holder for supporting the brush head mounting platform and accommodating a motor; wherein the brush head comprises bristles and a bristle implanting portion, and after being foamed the bristle bundles are radially distributed in a substantially evenly spaced manner across the surface of the bristle implanting portion, and wherein the bristles are soaked with a solvent or a solution for adsorbing and dissolving foreign substances or fouling when in use.

In accordance with the ninth aspect of the present disclosure, an electric orifice cleaning brush is provided, which comprises a brush head, a brush head mounting platform onto which the brush head is detachably mounted, and a motor holder for supporting the brush head mounting platform and accommodating a motor; wherein the brush head comprises bristles and a bristle implanting portion, the bristle implanting portion being substantially in the shape of a circular truncated cone, and after being formed the bristle bundles are radially distributed in a substantially evenly spaced manner across the surface of the bristle implanting portion, wherein there is no bristle bundles at the center region of the bristle implanting portion, such that an empty region is formed, the empty region comprising one or more apertures for facilitating air flowing; and wherein the motor drives the brush head assembly with a driving mechanism, a fan blade structure disposed on the driving mechanism being configured to rotate with the rotation of the driving mechanism, and produce a negative pressure upon the bristle implanting region through the apertures.

In accordance with the tenth aspect of the present disclosure, an electric orifice cleaning brush is provided, which comprises a brush head, a brush head mounting platform onto which the brush head is detachably mounted, and a motor holder for supporting the brush head mounting platform and accommodating a motor; wherein the brush head comprises bristles and a bristle implanting portion, the bristle implanting portion being substantially in the shape of a pillar structure, and after being formed the bristle bundles are distributed in a substantially evenly spaced manner across the surface of the bristle implanting portion.

The technical scheme in accordance with the present disclosure is capable of achieving complete cleaning of an orifice of a human body and avoiding damages to the orifice. The cleaning brush is convenient to operate and easy to replace. As such, it is suitable for medical applications.

BRIEF DESCRIPTION OF THE DRAWINGS

To more clearly describe the technical solutions of the embodiments of the present disclosure or prior art, in the following drawings used for illustrating the embodiments or prior art will be briefly described. Obviously, drawings used in the following description merely illustrate some embodiments of the present disclosure. And these drawings are not limitative to the present disclosure, but are illustrative.

DETAILED DESCRIPTION

In the following, reference will be made to the drawings of the embodiments of the present disclosure, to clearly and completely describe the technical solutions of the embodiments of the present disclosure. It is obvious that the embodiments as described are merely a part of but definitely not all embodiments of the present disclosure. All other embodiments obtained by a person skilled in the art, based on the embodiments, fall within the protection scope of the present disclosure, provided that obtaining these embodiments requires no creative work of such a person.

Figure 1:
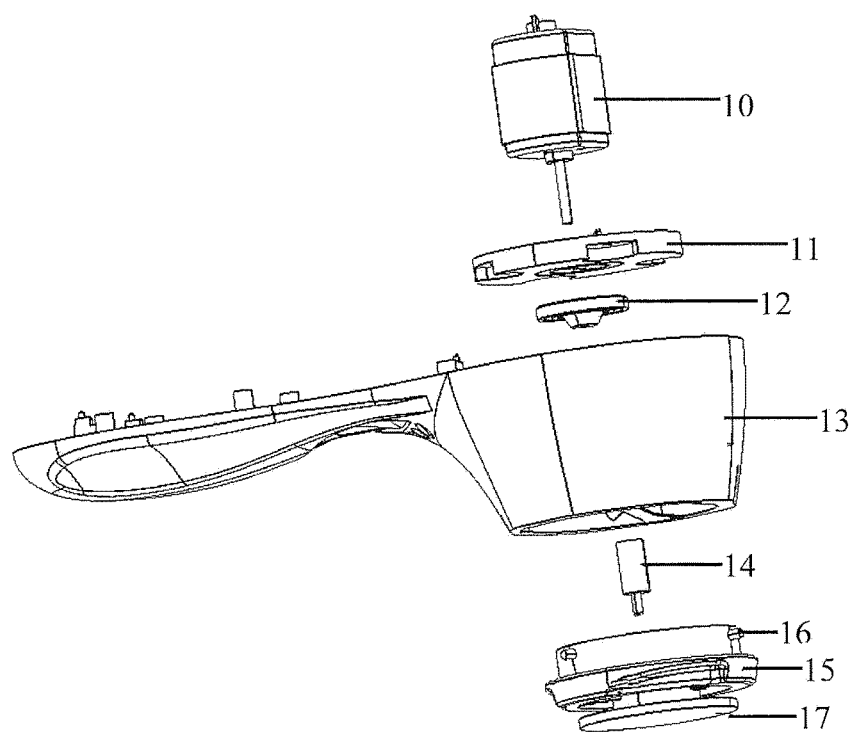
FIG. 1 is an exploded view of an electric orifice cleaning brush, in accordance with an embodiment of the present disclosure.
Figure 2:
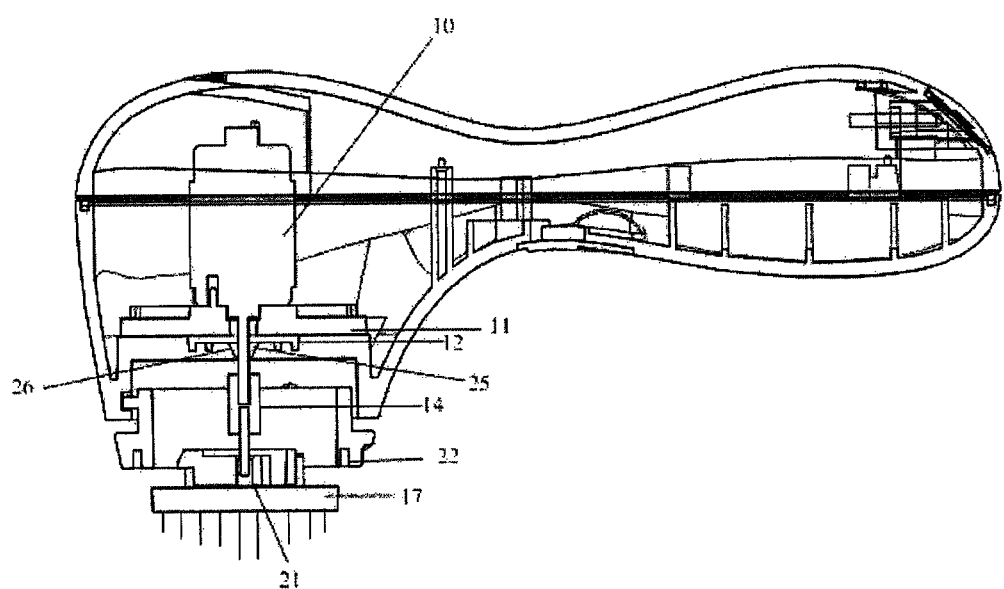
FIG. 2 is a side view of an electric orifice cleaning brush in accordance with an embodiment of the present disclosure.

FIGS. 1 and 2 are an exploded view and a side view, respectively, of an electric orifice cleaning brush in accordance with an embodiment of the present disclosure (bristles are not shown in FIG. 1). The orifice cleaning brush includes a motor 10, a motor holder 11, a sealing ring 12, an eccentric shaft 14, and a brush head assembly. The brush head assembly and the motor holder 11 are mounted onto the housing 13. A groove for accommodating the motor 10 is disposed on the motor holder 11. The motor 10 is fixed in the groove within the motor holder 11. The sealing ring 12 is located between the motor holder 11 and the housing 13.

There are holes disposed at the bottom central parts of the motor holder 11, the sealing ring 12, and the housing 13. When assembled, the driving shaft of the motor 10 successively penetrates through the holes on the motor holder 11, the sealing ring 12, and the housing 13, and its end extends outside the housing 13 and connects with one end of the eccentric shaft 14. The other end of the eccentric shaft 14 deviates from the center position and is connected to the brush head assembly as a the driving shaft for the brush head assembly.

In the present embodiment, the motor 10 connects with the brush head assembly through simple components such as the driving shaft and the eccentric shaft 14. The driving shaft of the motor 10 rotates and drives the eccentric shaft 14 to rotate, which in turn drives the brush head assembly to rotate. In this way, relevant energy loss is relatively low. The eccentric distance of the eccentric shaft is between 0.2 mm and 1 mm, for example, is 0.4 mm or 0.6 mm. Being driven by the driving shaft of the motor, the design of the eccentric shaft enables it to rotate around the driving shaft of the motor and to revolve on its own axis relative to other fixed components in the meantime. By way of a self-lubricating bearing 21, the eccentric shaft 14 is positioned at a bottom central groove of the brush head assembly. Therefore, it can cause the brush head assembly to move. However, it can be understood that, in other embodiments, the eccentric shaft 14 may be replaced by another eccentric component such as an eccentric wheel, and its another end may be connected to the brush head assembly after being connected to other transmission components.

As shown in FIGS. 1 and 2, the cleaning brush's brush shaft portion is substantially at a right angle to its brush head portion. However, it can be understood that, in other embodiments, it is also feasible that the cleaning brush's brush shaft portion is designed to be at an obtuse angle (such as an angle of 120 degrees, 135 degrees, or 150 degrees), or even at an angle of 180 degrees, to its brush head portion. In some applications, these designs may be convenient for an operator to use.

As shown in FIG. 2, the sealing ring 12 has a hollow structure, and both its inner side and its outer side take the form of disk structure 25. Its inner portion is a funnel-like hollow chamber 26, in which a lubricant is filled. This not only achieves lubrication of relevant components, but also ensures a complete insulation between the interior and exterior of the housing 13.

At its bottom central part, the housing 13 has a groove structure 19 matching with the structure of the sealing ring 12. Also, studs are disposed within the housing 13. Through the studs, the motor holder 11 can be fixed to the interior of the housing such that no fastener penetrating through the housing is required to fix the motor. In some embodiments, the number of the studs can be four.

The brush head assembly includes a brush head 15 and a brush head mounting platform 17 connected to the brush head 15. The brush head 15 includes an outer ring and an inner ring, which are connected with each other through an elastic soft connection 22. The outer ring of the brush head 15 can be fixed to the housing 13 via a pin mechanism. The bottom of the inner ring of the brush head 15 is provided with a self-lubricating bearing 21 connected to the driving shaft. The brush head 15 is detachably mounted onto the brush head mounting platform 17, and the mounting can be achieved through a snap-fit connection or a cladding, or any other suitable ways of installation. Of course, the brush head 15 can be integrally integrated onto the brush head mounting platform 17.

The existence of the elastic soft connection 22 makes the inner ring of the brush head 15 only rotates around the driving shaft, with minor or no revolving around its own axis. The self-lubricating bearing 21 between the driving shaft and the bottom groove of the brush head's inner ring also ensures that there can be only minor autorotation or no skidding-like autorotation of the brush head in response to the driving shaft's movement. Due to the eccentric shaft 14's function, the existence of the elastic soft connection 22 also enables the brush head to vibrate up-and-down and left-and-right.

In this embodiment, the motor 10 connects with the brush head assembly through its own driving shaft and the eccentric shaft 14. The rotation of the motor 10's driving shaft causes the eccentric shaft 14 to rotate. As the other end of the eccentric shaft 14 is coupled to the brush head assembly, the latter is also caused to rotate. In addition, the rotation is further converted by the elastic soft connection 22 into the up-and-down and left-and-right vibrations of the brush head 15.

Of course, it is possible to use a traditional driving mechanism that is so adopted that the rotation of the motor will cause the brush head 15 to rotate, instead of the eccentric shaft 14 and the elastic soft connection 22.

Figure 3A:
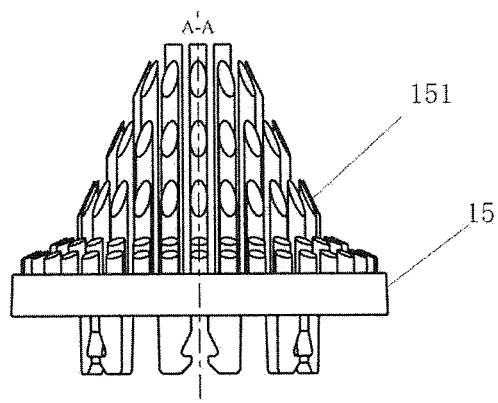
FIGS. 3A-3C illustrate a brush head in accordance with an embodiment of the present disclosure.
Figure 3B:
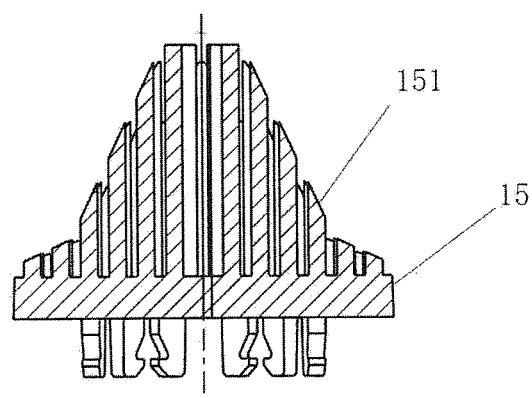
Figure 3C:
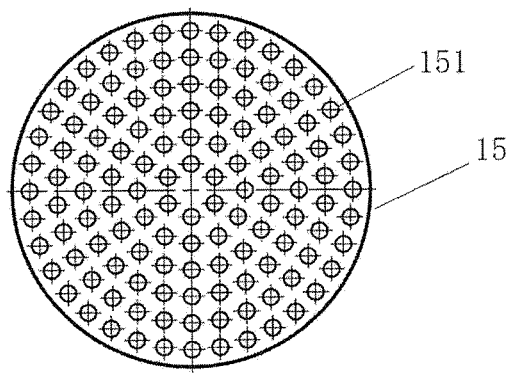

FIGS. 3A-3C illustrate a brush head in accordance with an embodiment of the present disclosure. FIG. 3A illustrates a front view of the brush head 15. FIG. 3B illustrates a longitudinal section of the brush head 15, the longitudinal section passing through the center axis A-A of the brush head. FIG. 3C illustrates a distribution of bristle bundles on the bristle implanting surface.

As shown in FIGS. 3A-3C, bristle bundles are substantially in the shape of a truncated cone in the longitudinal section. The bristle bundles are distributed in an evenly spaced manner across the bristle implanting surface. Starting from the center point of the bristle implanting surface, these bristle bundles are distributed radially, and on the whole embody a plurality of concentric circular rings. Of course, it should be understood that the bristle bundles also can be distributed in the form of concentric square rings.

As shown in FIG. 3C, the distance between the bristle bundles is about 2.7 mm. It should be understood that the distance can be set to be within a range of 1.5 mm to 3.5 mm.

As shown in FIGS. 3A-3C, the heights of the bristle bundles are gradually lowered along the radial direction, from the center of the bristle implanting surface to outside. This is to clean the deep regions of an umbilical hole. Referring to FIG. 3A, on the ring closest to the center of the bristle implanting surface, the height of the highest bristle bundle is around 22 mm, while after gradual reduction in height, the height of the bristle bundles on the outermost ring is around 3 mm. Also, the heights of the bristle bundles are gradually lowered from the interior to the exterior at different slopes. In regions adjacent to the center region, the slope of height reduction is relatively higher and is around 2.14, while in peripheral regions the slope of height reduction is abruptly decreased and is around 0.42. It should be understood that these designs are mainly made to match with the ergonomic structure of an umbilical hole. In other embodiments, other heights and slopes may be adopted.

When a cleaning brush is being normally used, it is mainly bristles located at its center region that contact the skin of a person to be cleaned, and bristles with smaller heights located at peripheral region does not contact the skin. However, considering that some unintended contact may be made in the course of cleaning, bristles located at peripheral regions may contact the skin of the person to be cleaned occasionally. At that moment, bristles located at peripheral regions may serve as a bumper to avoid the discomfort caused by those people with highly sensitive skin directly contacting the structural components of the brush head, which are typically made from metals or plastics.

It can be learned from FIGS. 3A and 3B that, in the present embodiment, the tips of bristle bundles are rounded and blunted. The resulting shape lowers the irritation that may be made to a human body. Of course, in some embodiments, the tips of bristle bundles are not modified and retain their natural shapes.

In the present embodiment, the bristle's material can be nylon fiber. However, pig hair or wool may be selected according to actual needs. These materials have different softness and can be used for cleaning people at different ages. For example, softer bristles may be more suitable for infants.

Though not shown, it should be understood that, the bristle bundles need to be implanted into the bristle implanting portion at a certain depth. For example, the implanting depth may be 3 mm, which can ensure that bristles are not easily detached from the bristle implanting portion. A greater implanting depth also can be contemplated. However, the size of the bristle implanting portion as well as the size of the whole brush head need to be considered, too. As described in the above, in other embodiments, it is possible to set the cleaning brush's brush shaft portion to be at an obtuse angle (for example 120 degrees, 135 degrees, or 150 degrees), or even an angle of 180 degrees, to its brush head portion, which may be more convenient for some operators to use and allow the brush head portion to have large dimensions (especially in depth). Thus larger bristle implanting depths may be conceivable.

In some embodiments, bristles may be stuck in bristle implanting holes after being bent by metal sheets. In some embodiments, to prevent detachment of bristles, glue is used at the implanted portions of the bristle bundles to bond bristles. In addition, in some embodiments, at the opening of each bristle implanting hole and over the bristle implanting surface, an elastic hoop (not shown) is provided to compact the bristle bundle.

In some embodiments, bristles are made from materials which are inherently colorful. Those vivid colors which are distinct from the skin color, such as red, blue, etc., may be selected. As such, even some bristles are detached in an operation, they will be easily discernible, which makes it convenient for medical care personnel to get rid of these bristles quickly, without causing secondary contamination. Of course, colorful bristles are also more aesthetically pleasing.

In some embodiments, silica gel material can be used to make bristles such that each individual bristle constitutes a bristle bundle. It can be understood that, in this situation, the bristles and the bristle implanting portion can be integrally formed. One advantage of using silica gel material is to better cater to the sensitive skins of some people to be cleaned.

In addition, in some embodiments, when in use bristles may be soaked with certain solvents or solutions (for example iodophor, alcohol, turpentine, etc.). These solvents or solutions may help dissolve matters to be cleaned off (e.g., foreign substances, fouling, etc.) and adsorb them onto bristles.

Figure 4A:
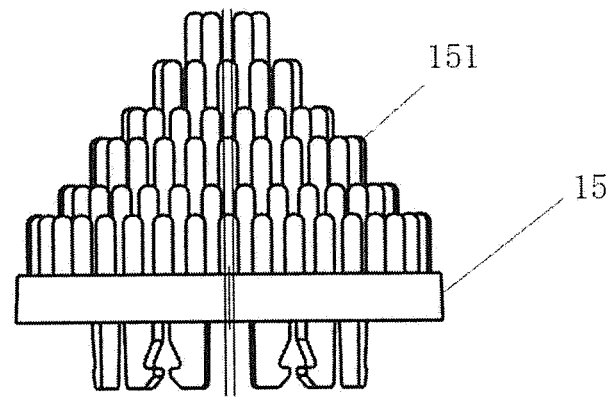
FIGS. 4A and 4B illustrate a brush head in accordance with another embodiment of the present disclosure.
Figure 4B:
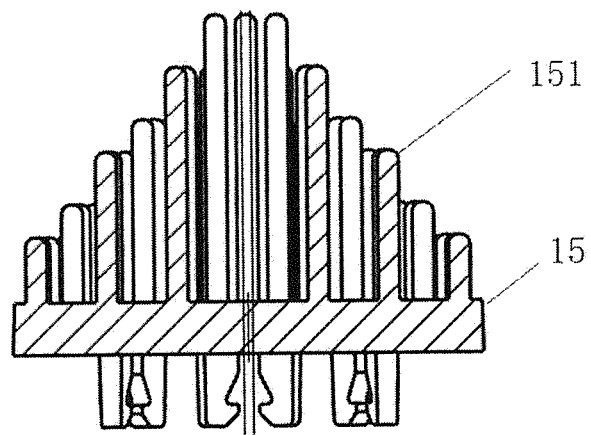

FIGS. 4A-4B illustrate a brush head in accordance with another embodiment of the present disclosure. FIG. 4A illustrates a front view of the brush head, and FIG. 4B illustrates the brush head's longitudinal section, which passes through the center axis of the brush head.

As shown in FIGS. 4A-4B, the bristle bundle 151 is substantially in the shape of a truncated cone in the longitudinal section. The heights of the bristle bundles 151 are gradually lowered along the radial direction, from the center of the bristle implanting portion to outside. Referring to FIG. 4A, the heights of the bristle bundles 151 are gradually lowered from the interior to the exterior according to a substantially uniform slope. Specifically, on the ring closest to the center of the bristle implanting surface, the height of the highest bristle bundle is around 22 mm. While after being gradually lowered, the height of the bristle bundle located on the outermost ring is about 5 mm.

Figure 5:
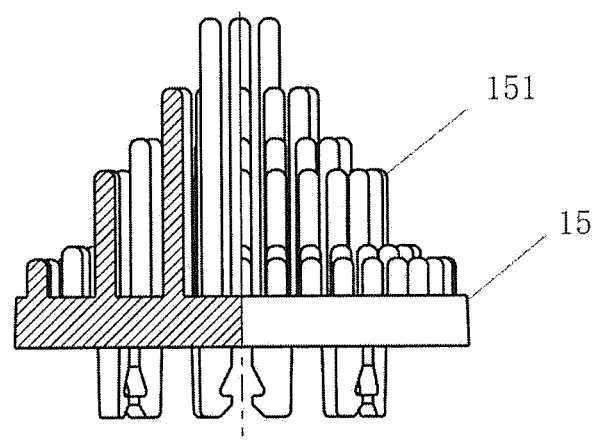
FIG. 5 illustrates a brush head in accordance with still another embodiment of the present disclosure.

FIG. 5 illustrates a brush head in accordance with still another embodiment of the present disclosure. The left portion of FIG. 5 illustrates a longitudinal section of the brush head, and the right portion of FIG. 5 illustrates a front view of the brush head.

Being similar to the embodiment as shown in FIGS. 4A-4B, the bristle bundles 151 of FIG. 5 are substantially in the shape of a truncated cone in the longitudinal section. Their heights are gradually lowered along the radial direction, from the center of the bristle implanting surface to outside, and the rate of height reduction is substantially uniform. However, it is slightly different that the heights of some bristles are not lowered according to a uniform slope, but are lowered step by step.

Figure 6:
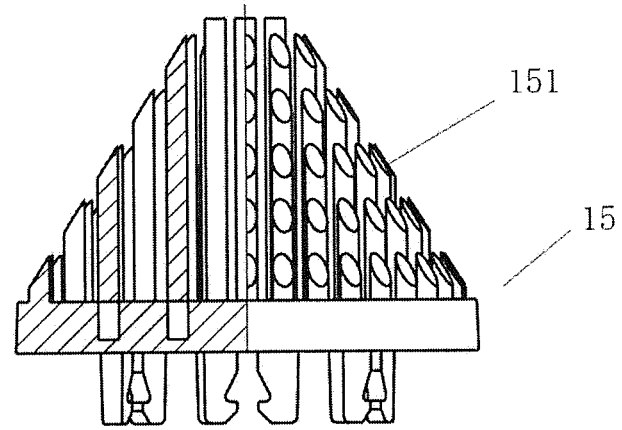
FIG. 6 illustrates a brush head in accordance with yet another embodiment of the present disclosure.

FIG. 6 illustrates a brush head in accordance with yet another embodiment of the present disclosure. The left portion of FIG. 6 illustrates a longitudinal section of the brush head, and the right portion of FIG. 6 illustrates a front view of the brush head.

Being similar with the embodiment as shown in FIGS. 3A-3B, the bristle bundles 151 of FIG. 6 are substantially in the shape of a truncated cone in the longitudinal section. Their heights are gradually lowered along the radial direction, from the center of the bristle implanting surface to outside. However, the slope of height reduction is uniform, and the slope is about 1.6.

Figure 7:
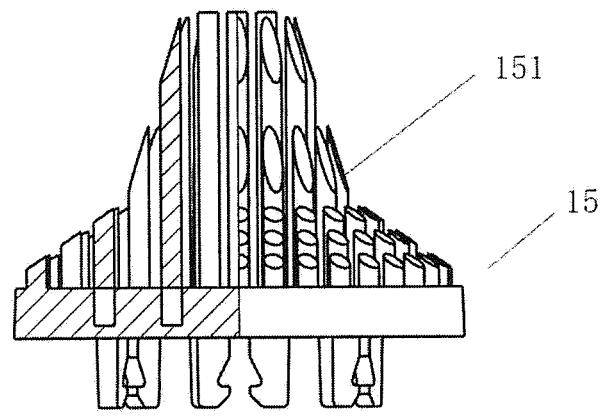
FIG. 7 illustrates a brush head in accordance with yet another embodiment of the present disclosure.

FIG. 7 illustrates a brush head in accordance with another embodiment of the present disclosure. The left portion of FIG. 7 illustrates a longitudinal section of the brush head, and the right portion of FIG. 7 illustrates a front view of the brush head.

Being similar with the embodiment as shown in FIGS. 3A-3B, the bristle bundles 151 of FIG. 7 are substantially in the shape of a truncated cone in the longitudinal section. Their heights are gradually lowered along the radial direction, from the center of the bristle implanting surface to outside. However, the slope of height reduction is not uniform. Specifically, the slope of height reduction is relatively higher and is about 3.27 in regions close to the center region, while at peripheral regions the slope of height reduction is abruptly decreased to about 0.7. Such a slope design may better match with the shapes of umbilical holes of some people to be cleaned.

Figure 8:
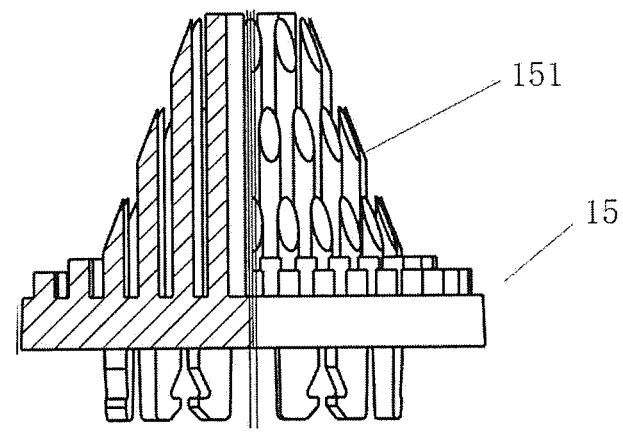
FIG. 8 illustrates a brush head in accordance with yet another embodiment of the present disclosure.

FIG. 8 illustrates a brush head in accordance with still another embodiment of the present disclosure. The left portion of FIG. 8 illustrates a longitudinal section of the brush head; and the right portion of FIG. 8 illustrates a front view of the brush head.

Being similar with the embodiment as shown in FIGS. 3A-3B, the bristle bundles 151 of FIG. 8 are substantially in the shape of a truncated cone in the longitudinal section. Their heights are gradually lowered along the radial direction, from the center of the bristle implanting surface to outside. However, the slope of height reduction is not uniform. Specifically, the slope of height reduction is relatively higher and is about 2.6 in regions close to the center region, while at peripheral regions the slope of height reduction is not decreased according to a slope, but is decreased step by step in a moderate manner.

Figure 9:
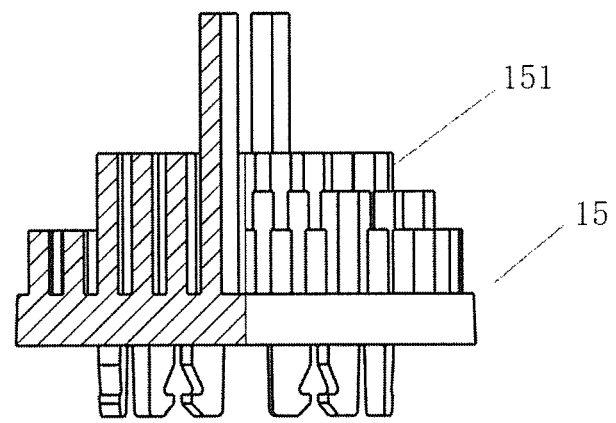
FIG. 9 illustrates a brush head in accordance with yet another embodiment of the present disclosure.

FIG. 9 illustrates a brush head in accordance with another embodiment of the present disclosure. The left portion of FIG. 9 illustrates a longitudinal section of the brush head, and the right portion of FIG. 9 illustrates a front view of the brush head.

The bristle bundles of FIG. 9 are substantially in the shape of a superposition of a plurality of truncated cones. The heights of bristle bundles 151 are gradually lowered along the radial direction, from the center of the bristle implanting surface to outside, and are decreased step by step. The height differences between bristle bundles located closer to the interior are relatively bigger, while the height differences between bristle bundles located closer to the exterior are relatively smaller.

Figure 10:
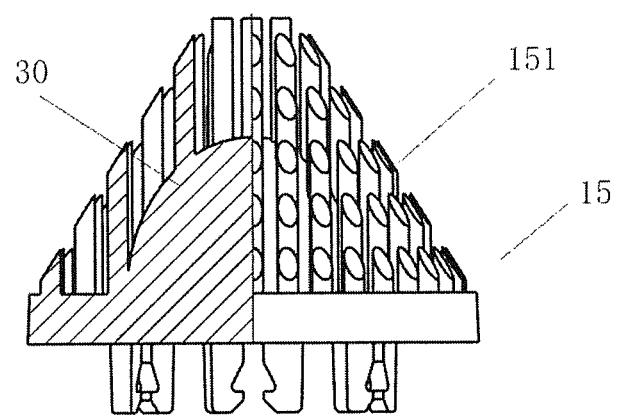
FIG. 10 illustrates a brush head in accordance with yet another embodiment of the present disclosure.

FIG. 10 illustrates a brush head in accordance with another embodiment of the present disclosure. The left portion of FIG. 10 illustrates a longitudinal section of the brush head, and the right portion of FIG. 10 illustrates a front view of the brush head.

The bristle implanting surface of FIG. 10 is not made level and flat. Instead, there is a protrusion 30 disposed at the center region of the bristle implanting portion. As such, the lengths of the exposed portions of the bristle bundles 151 located at the center region are shortened. In the case of same material being used, the hardness of this part of bristles will be increased, which may further enhance its cleaning capability. Referring to FIG. 10, the protrusion 30 is in the shape of a circular arch, which may help match with the overall truncated cone shape of the bristle bundles. It should be understood that, protrusions having other shapes, such as having a truncated cone shape, a multi-step shape, or a cylindrical shape, may be feasible, too.

Referring again to FIG. 3C, in this embodiment, there is no bristle bundle disposed at the center region of the bristle implanting surface, thus an empty region without bristles is formed at the center region. As there is no bristle bundle disposed at the center region, it is not necessary to provide holes at this region of the bristle implanting portion of the brush head. As such, the firmness of the center region can be ensured so that it is not easy for the center region to get broken. In addition, when the cleaning brush is being used, especially in an embodiment of the brush head rotating with the motor, a certain level of negative pressure may be produced at the empty region, which is conducive to adsorbing those substances to be cleaned off to the bristles.

Figure 11:
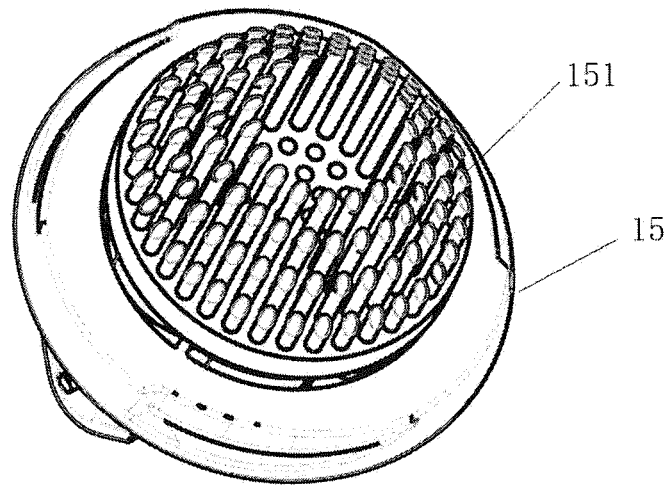
FIG. 11 is a schematic view of a brush head in accordance with an embodiment of the present disclosure.

FIG. 11 is a schematic view of a brush head in accordance with an embodiment of the present disclosure. In this embodiment, there is no bristle bundle disposed at the center region of the bristle implanting surface. However, one or more apertures are still provided at the center region. The sizes of these apertures may be equal to the sizes of those bristle implanting holes. In some embodiments, the sizes of these apertures may be designed to be smaller. The diameters of these apertures may be contemplated to both increase the negative pressure and ensure a certain level of firmness of the structure.

Figure 12:
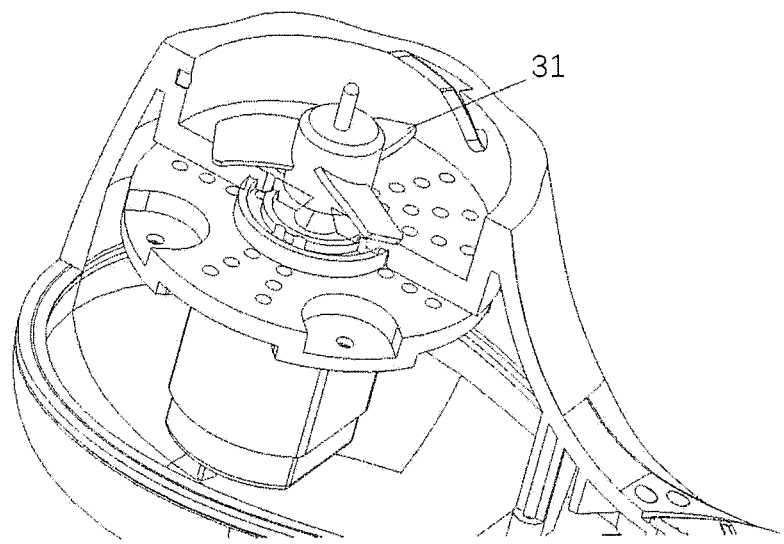
FIG. 12 is a partial view of a cleaning brush in accordance with an embodiment of the present disclosure.

FIG. 12 is a partial section view of a cleaning brush in accordance with an embodiment of the present disclosure. It can be seen that small-sized fan blades 31 are disposed on the driving shaft of the motor. Unlike a traditional fan, which is blowing forward at the time of rotation, the curved shape and curvature of the fan blades 31 are designed to blow backward (i.e., suck the air ahead) at the time of rotating with the driving shaft. As such, in rotation the fan blades 31 may produce a negative pressure in the central empty region through the apertures, thereby facilitating adsorbing those substances to be cleaned off. In some embodiments, several apertures are disposed on the housing of the motor holder as well, so as to facilitate air flowing.

Of course, it should be understood that, as the eccentric shaft is capable of rotating, too, in some instances, the fan blades 31 may be disposed on the eccentric shaft 14.

Figure 13:
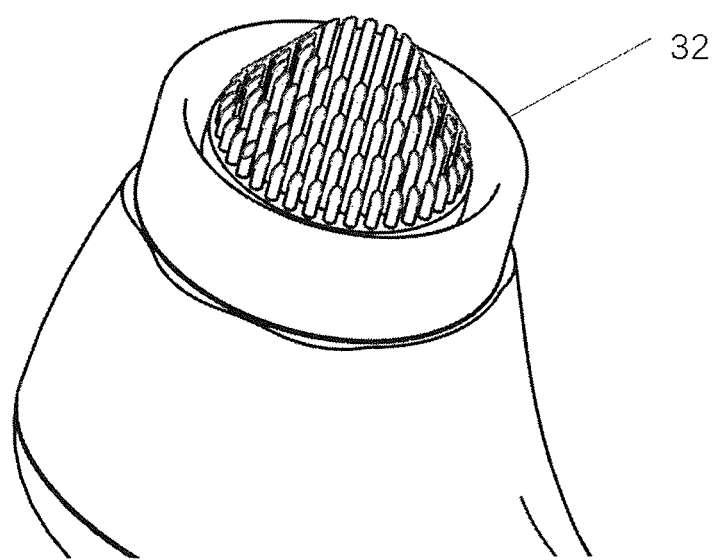
FIG. 13 is a partial view of a cleaning brush in accordance with another embodiment of the present disclosure.

Referring to FIG. 13, it is a partial view of a cleaning brush in accordance with another embodiment of the present disclosure. In this embodiment, there is a rigid sleeve 32 disposed at the peripheral part of the brush head. For some people to be cleaned, as their umbilical holes may be relatively deep, it may be difficult to contact the skins deep in these umbilical holes by directly using soft bristles. By this rigid sleeve 32, the umbilical holes may be spread, such that the deep portions now become shallower, and thus easier to be cleaned. This rigid sleeve may be made of a transparent material, such as a tempered glass, as this will help the operator to see what kind of contact is achieved between bristles and the skin of the patient.

In some embodiments, the bristle implanting portion is made to be movable to enable it to be extendable and retractable within the rigid sleeve, so as to achieve a better contact with a patient's skin. Of course, it should be understood that this also can be achieved by designing the rigid sleeve as a movable component. For example, the sleeve is slidably fit over the peripheral part of the brush head, by means of one or more bumps, where different positions of the bumps define different lengths that the sleeve may extend forward. The bumps may be disposed on the inner side of the sleeve, or on the peripheral part of the brush head.

Figure 14:
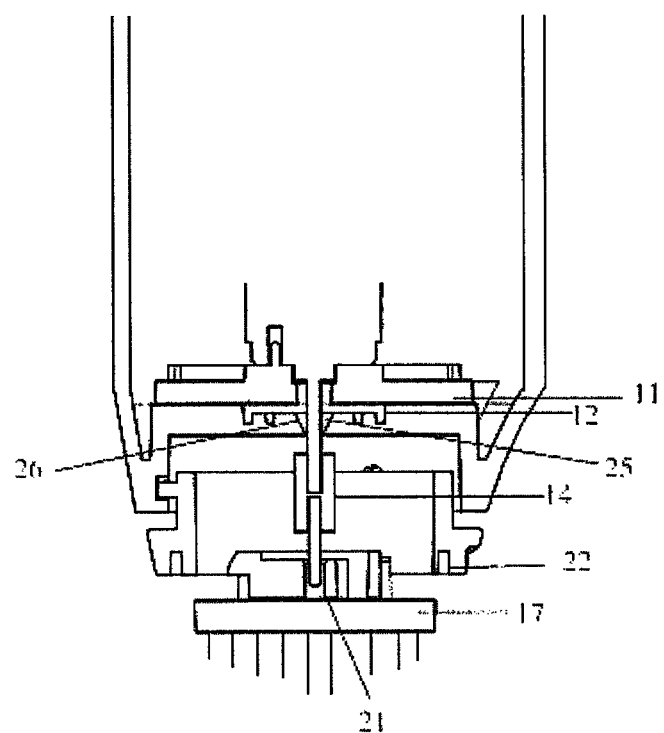
FIG. 14 is a partial view of a cleaning brush in accordance with still another embodiment of the present disclosure.

FIG. 14 is a partial view of a cleaning brush in accordance with an embodiment of the present disclosure. In this embodiment, the brush shaft portion of the cleaning brush is set to be at an angle of 180 degrees to its brush head portion. As such, a user may hold the cleaning brush like holding a pen. In these embodiments, the diameters of the brush shaft portion and the brush head portion need to be designed to be correspondingly smaller, so as to be convenient for a user to hold. These pen-like embodiments are especially suitable for cleaning relatively small orifices such as ear holes or nostrils.

Figure 15:
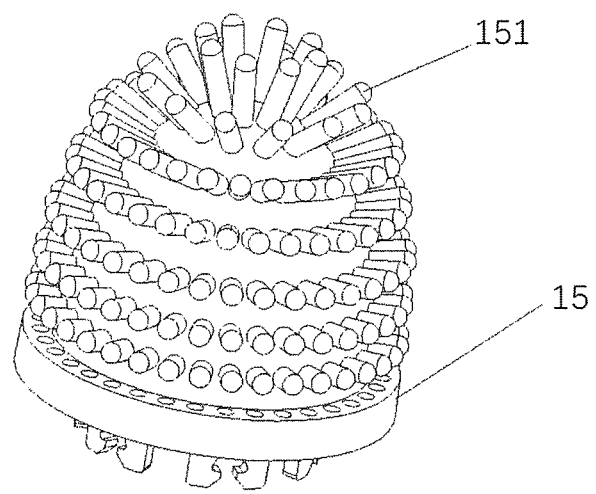
FIG. 15 illustrates a brush head in accordance with yet another embodiment of the present disclosure.

FIG. 15 illustrates a brush head in accordance with yet another embodiment of the present disclosure. In this embodiment, the bristle implanting portion is designed to be in the shape of a pillar structure, and bristles are substantially evenly distributed on the surface of the pillar structure. The bristle implanting portion with a pillar structure is particularly suitable for a pen-like cleaning brush. When cleaning relatively deep orifices with relatively small diameters (such as ear holes and nostrils), such a shape is especially convenient for a user to operate. However, it should be understood that, it is also feasible to use a bristle implanting portion with a pillar structure in cleaning brushes of other shapes. In some embodiments, the end of the pillar bristle implanting portion facing a patient's skin is not flat, but dome-like, which makes the spatial distribution of bristles to be more uniform. In some embodiments, bristles used have multiple colors and bristles of different colors are distributed along the longitudinal direction of the pillar structure, which can serve as an intuitive prompt to a user as to how deep have the bristles gone into the patient's orifice (such as an ear hole, a nostril, etc.).

Above description of the disclosed embodiments enables a person skilled in the art to implement or use the present disclosure. It should be understood that, except for specially described situations, the disclosed features of above embodiments may be used alone or in combination. Various modifications to these embodiments will be obvious to a person skilled in the art. The general principle as defined herein may be carried out in other embodiments, without departing from the spirit or scope of the present disclosure. Therefore, the present disclosure as disclosed herein is not limited by the disclosed specific embodiments, but is intended to cover those modifications falling within the spirit and scope of the present disclosure, as defined by appended claims.

What is claimed is:

1. An electric orifice cleaning brush, comprising:
   a brush head;
   a brush head mounting platform onto which the brush head is detachably mounted; and
   a motor holder for supporting the brush head mounting platform and accommodating a motor, wherein:
   the brush head comprises:
      a bristle implanting portion in the shape of a truncated cone and comprising a center region, and
      bristles formed in bristle bundles, the bristle bundles being disposed outside, but not inside, the center region of the bristle implanting portion so that an empty space is formed in the center region, wherein the bristle bundles are radially distributed in an evenly spaced manner; and
   the motor is configured to drive the brush head to vibrate up and down to generate a negative pressure in the empty space in the center region of the bristle implanting portion.

2. The cleaning brush in accordance with claim 1, wherein the brush head comprises a protrusion disposed at the center region of the bristle implanting portion.

3. The cleaning brush in accordance with claim 2, wherein there is no hole disposed at the center region of the bristle implanting portion.

4. The cleaning brush in accordance with claim 2, wherein the protrusion and the bristle implanting portion are integrally formed.

5. The cleaning brush in accordance with claim 2, wherein
   the bristle implanting portion further comprises a peripheral region, and
   at least one of the bristle bundles is disposed at the peripheral region of the bristle implanting portion.

6. The cleaning brush in accordance with claim 1, wherein the bristles are soaked into a solvent or a solution for adsorbing and dissolving matters to be cleaned off when in use.

7. The cleaning brush in accordance with claim 1, wherein the heights of the bristle bundles are gradually lowered along the radial direction from the center of the bristle implanting portion.

8. The cleaning brush in accordance with claim 7, wherein the magnitude of reduction in the heights of the bristle bundles is uniform.

9. The cleaning brush in accordance with claim 7, wherein the magnitude of reduction in the heights of the bristle bundles is gradually decreased.

10. The cleaning brush in accordance with claim 1, wherein the cleaning brush is used for medical cleaning.

11. The cleaning brush in accordance with claim 10, wherein the cleaning brush is used for cleaning an orifice of a human body.

12. The cleaning brush in accordance with claim 1, wherein the motor is further configured to drive the brush head to rotate to generate further negative pressure in the center region of the bristle implanting portion.

13. The cleaning brush in accordance with claim 12, wherein one or more apertures are disclosed in the center region of the bristle implanting portion for increasing the negative pressure.

14. The cleaning brush in accordance with claim 13, wherein a size of each of the one or more apertures is the same as a size of each of holes in which the bristles are disposed.

15. The cleaning brush in accordance with claim 13, wherein a size of each of the one or more apertures is smaller than a size of each of holes in which the bristles are disposed.

16. The cleaning brush in accordance with claim 13, further comprising:
   one or more fan blades configured to rotate with rotation of the motor to facilitate the generation of the negative pressure in the center region of the bristle implanting portion through the one or more apertures.

* * * * *